United States Patent [19]
Bachmann

[11] Patent Number: 5,133,198
[45] Date of Patent: Jul. 28, 1992

[54] ENDOSCOPIC APPARATUS FOR FLAW DETECTION ON A CIRCULAR KNITTING MACHINE

[75] Inventor: Jean-Marie Bachmann, Saint Julien Les Villas, France

[73] Assignee: Institut Textile De France, France

[21] Appl. No.: 578,735

[22] Filed: Sep. 6, 1990

[30] Foreign Application Priority Data

Sep. 15, 1989 [FR] France .................. 89 12296

[51] Int. Cl.$^5$ .............. D04B 35/20; G01N 21/00
[52] U.S. Cl. ..................................... 66/166; 356/241
[58] Field of Search ............. 66/166, 252; 356/237, 356/238, 241

[56] References Cited

U.S. PATENT DOCUMENTS

| | | |
|---|---|---|
| 3,116,621 | 1/1964 | Klein et al. .................. 66/166 |
| 3,3345,836 | 10/1967 | Fertig et al. ................. 66/166 |
| 3,761,186 | 9/1973 | Wason ......................... 256/241 |
| 4,248,533 | 2/1981 | Shimada ....................... 356/238 |
| 4,440,496 | 4/1984 | Milana ........................ 356/241 |
| 4,464,913 | 8/1984 | Rosenquist et al. ............ 66/166 |
| 4,748,334 | 5/1988 | Kobayashi et al. ............. 66/166 X |
| 4,820,043 | 4/1989 | Diener ........................ 356/241 |
| 4,860,559 | 8/1989 | Hill .......................... 66/232 X |

FOREIGN PATENT DOCUMENTS

| | | |
|---|---|---|
| 0310838 | 4/1989 | European Pat. Off. .......... 66/166 |
| 2644502 | 4/1977 | Fed. Rep. of Germany ........ 66/166 |
| 2843653 | 4/1980 | Fed. Rep. of Germany ........ 66/166 |
| 3536991 | 1/1987 | Fed. Rep. of Germany . |
| 4001650 | 8/1990 | Fed. Rep. of Germany ........ 66/166 |
| 1258054 | 11/1986 | Japan ......................... 66/232 |
| 1183563 | 7/1989 | Japan ......................... 66/166 |

OTHER PUBLICATIONS

Jcehnk, "Indentification et determination automatiques des defauts de tissage," L'Industrie Textile, No. 1067, pp. 277 to 279.

Primary Examiner—Werner H. Schroeder
Assistant Examiner—John J. Calvert
Attorney, Agent, or Firm—Ladas & Parry

[57] ABSTRACT

The apparatus has particular use in the detection of flaws in articles being knitted on a circular knitting machine and aplies in particular to the manufacturing of footwear. The apparatus comprises a light source, an electro-optical sensor receiving light coming from the light source after the light has been reflected by the knitted fabric, or after it has passed through that knitted fabric. Devices are provided for processing the data produced by the electro-optical sensor. According to the invention, there is provided a linear endoscope fixedly mounted along the rotation axis of the machine, whose viewing cone is matched to a distal lens and is oriented radially towards the knitted fabric. The photosensitive zone of the electro-optical sensor is located at the image plane of a lens located at a proximal end of the endoscope.

11 Claims, 3 Drawing Sheets

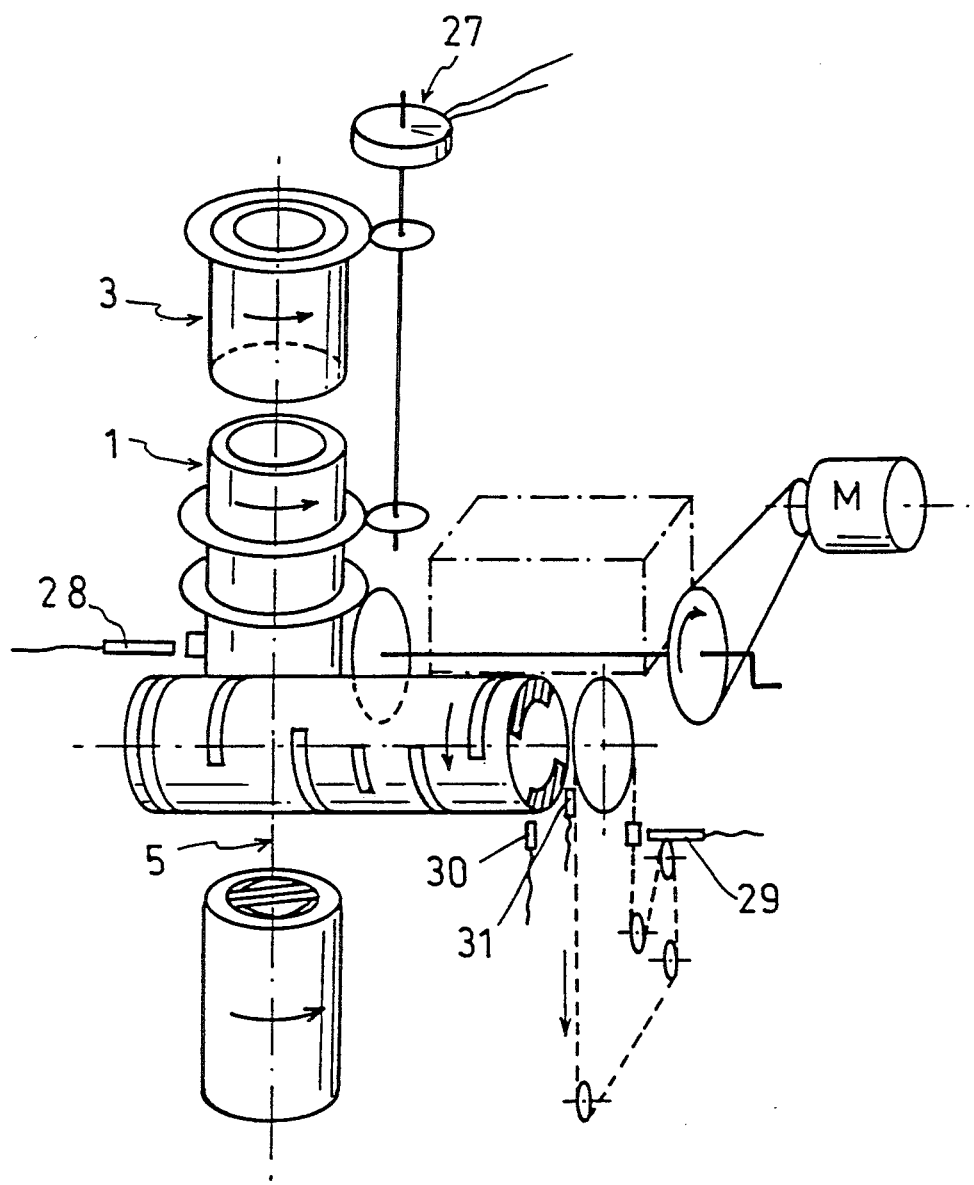
FIG_5

ENDOSCOPIC APPARATUS FOR FLAW DETECTION ON A CIRCULAR KNITTING MACHINE

BACKGROUND OF THE INVENTION

1. Field of the Invention

The present invention relates to an apparatus for the optical detection of flaws in articles as they are being knitted in a circular knitting machine, and in particular to an apparatus for detecting flaws in footwear, irrespective of whether such flaws arise from faults in the knitting process or from various other origins e.g. the presence of yarns that are too thick or too thin, or from faults in the plaiting.

2. Prior Art

Flaw detection systems for fabrics based on optical inspection have already been proposed in the prior art. Such systems are described e.g. the publication "L'Industrie Textile" No. 1067 pages 277 to 279. They comprises a luminous source, an electro-optical sensor receiving light from the optical source after it has either been reflected from or passed through, the fabric, and means for processing data from the electro-optical sensor. The fabric is laid out flat and made to pass in front of tubular fluorescent lamps powered by a DC voltage source in order to illuminate the fabric throughout its width. Electro-optical cells are aligned along a row and extend throughout the width of the fabric. The lamps and the cells are either both on the same side of the fabric or on either side. In the first case, the cells measure the light reflected by the fabric. In the second case they measure the light passing through the fabric. Any change in the fabric's structure or surface condition resulting from flaws in the weaving or in the dressing brings about a change in the current of the photoelectric cell concerned, so triggering a signal which is amplified by an amplifier and sent to an analog-digital converter for subsequent processing. By using adjustable thresholds it is possible to set the level of the signal that qualifies as a flaw indication.

The flaw inspection systems for fabrics described in the above article are not readily amenable to the detection of flaws in articles being knitted in a circular knitting machine and even less so in the case of knitting machines having a small diameter, as used in the manufacture of items of footwear. The reason is that in such machines, the knitted fabric is produced by a rotation of the knitting head and is then passed around a mandrel such that the part of the knitted fabric open to inspection is very difficult to access.

SUMMARY OF THE INVENTION WITH OBJECTS

The present invention has for object an optical device for flaw detection that overcomes the above-mentioned drawbacks and makes it possible to detect flaws in articles being knitted on a circular knitting loom, including small-diameter knitting looms as used in the manufacture of items of footwear. In common with other known devices, the apparatus of the present invention comprises a luminous source, an electro-optical sensor receiving light from the source after it has been reflected by the knitted fabric, or alternatively after it has passed through the knitted fabric, and means for processing data produced by the electro-optical sensor.

According to the invention, the apparatus comprises a linear endoscope fixedly mounted along a rotation axis of the loom and having a viewing cone matched to a lens at a distal end of the endoscope and oriented radially towards the knitted fabric. Furthermore the photosensitive zone of the electro-optical sensor is situated substantially in the image plane of a lens located at a proximal end of the endoscope.

An endoscope is a device, used e.g. in the medical field, which comprises an optical system having a succession of lens elements whereby an optical inspection can be performed at a precise zone. Endoscopes usually have means for bringing a luminous flux after reflection from the inspection zone and for retrieving the part of this flux reflected from the zone. The distal end corresponds to the end placed close to the inspected zone, while the proximal end corresponds to the end from which the incident luminous flux is sent and/or where the reflected flux is returned.

Thus, the endoscope used in the context of the present invention is complementary to the optical flaw detection apparatus and plays an essential role in exploring a precise part of the knitted fabric, this part preferably being close to the needles associated with the machine, i.e. where the knitted fabric is in a uniformly stretched state. The endoscope also has the function of re-directing the luminous flux to a more accessible part of the machine after inspection of the knitted fabric.

According to a first embodiment, the luminous source comprises light producing means and an optical fiber terminated by a totally relecting prism, the optical fiber being fixedly mounted within a cylinder of the machine and close to a wall thereof, and the prism being radially oriented towards the distal lens of the endoscope. In this first embodiment, the luminous flux received by the electro-optical sensor corresponds to light filtered by the corresponding zone of the knitted fabric. This transmissive illumination mode makes it possible to detect certain types of flaws—holes, thin or thick zones—by back lighting.

In a second embodiment, the endoscope is used conventionally whereby the luminous flux from the light producing means is conveyed within the endoscope from its proximal end to its distal end. According to this embodiment, the endoscope serves both as a luminous source and as a means for conveying the light reflected from the inspected zone of the knitted fabric. This reflective illumination mode makes it possible to reveal flaws that have a good luminous contrast: spurious presence of colored strands, and faults in the pattern or plaiting.

Preferably, the two above-mentioned embodiments are combined on a same knitting machine. In this case the inventive apparatus comprises two light sources, one for illumination by transmission and the other for illumination by relection. Switching means are provided for switching alternately from one source to the other. In this way, the endoscope alternately conveys a transmitted luminous flux and a relected luminous flux to the electro-optical sensor, so making it possible to detect all of the above-mentioned types of flaw.

The means for processing the data from the electro-optical sensor comprise synchronization means capable of sampling at a frequency that is slaved to the rotation of the knitting machine, such that successive inspection zones on the knitted fabric overlap both in the direction of the columns and in the direction of the rows. This guarantees a total inspection of a tubular knitted fabric without any loss of information.

The synchronization means can e.g. comprise a count-up encoder supplying a predetermined number of pulses during each rotation of the machine for sampling the analog signal delivered by the electro-optical sensor, a proximity detector supplying a fast signal at the beginning of a row, a detector synchronized with a knitting program for resetting the apparatus at the first stitch of the knitted article, and means for informing the apparatus of the beginning and end of the alternating movement of the machine, corresponding to the heel and toe sections in the case of an item of footwear. The latter means may be either sensors or signals produced as a function of the knitting programme. The electro-optical sensor may e.g. be a photodiode having a response curve matched to the wavelength of the luminous source.

BRIEF DESCRIPTION OF THE DRAWINGS

Other characteristics and advantages of the present invention shall become more apparent upon reading the following description of the preferred embodiments, given with reference to the appended drawings in which:

FIG. 5 is a general schematic view of a circular knitting machine for items of footwear equipped with synchronizing means.

DESCRIPTION OF THE PREFERRED EMBODIMENTS

Figure 1:
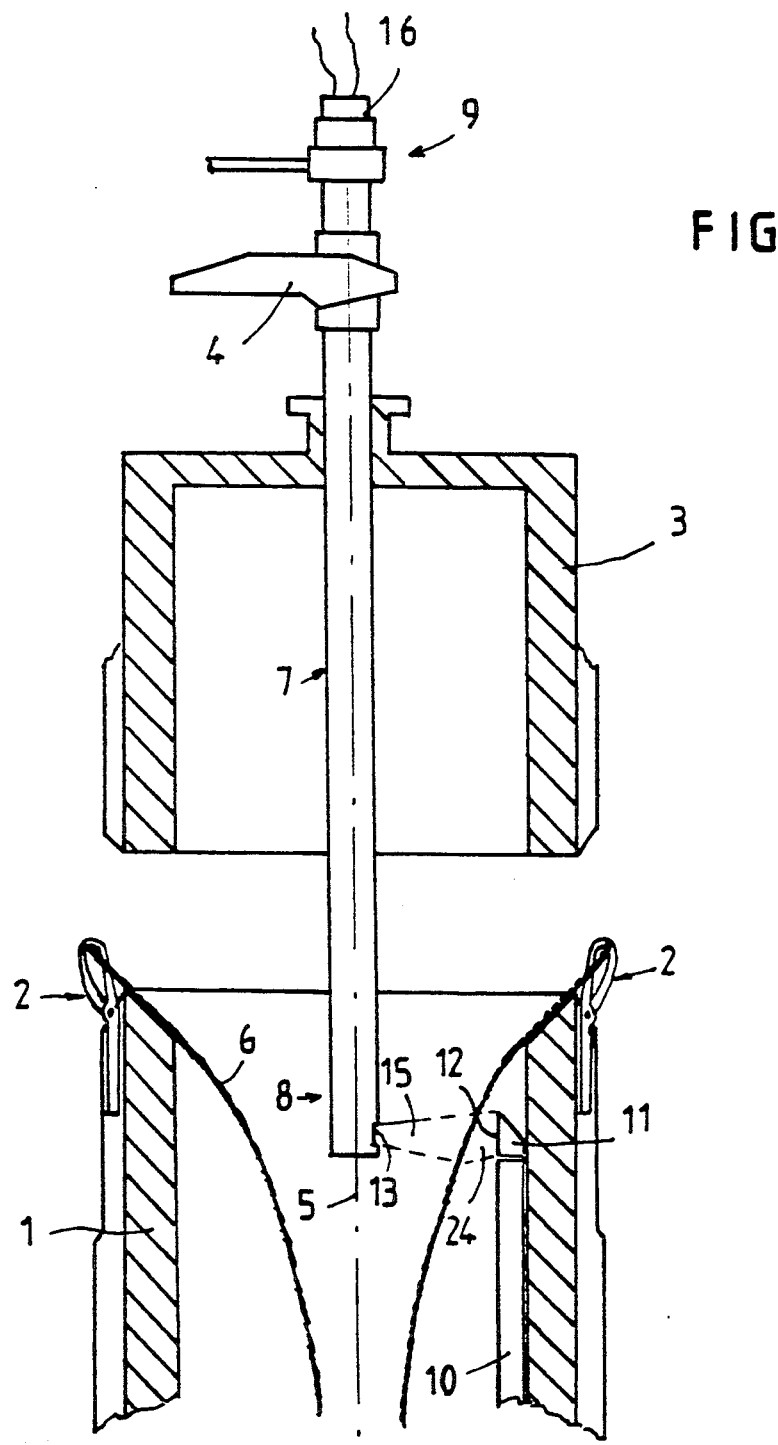
FIG. 1 is a schematic cross-sectional view of a knitting machine for items of footwear equipped with an endoscopic device having two light sources.

A knitting machine for socks, e.g. of the double-cylinder type, is depicted very schematically in FIG. 1. The hatched portions correspond to a cross sectional view of the machine upper cylinders 1 and lower cylinders 3. These cylinders have longitudinal grooves in which needles are slidably engaged. The needles have a symmetrical configuration for a double-cylinder machine, can operate in the lower cylinder, as shown in FIG. 1, or alternatively in the upper cylinder.

Cylinders 1 and 3 are controlled in rotation around axis 5. In the course of knitting, the sock having a tubular shape 6, is suspended from the needles 2 and drawn inside the cylinder 1 by an extraction device (not shown).

The endoscope 7 is rectilinear and fixedly mounted along the rotation axis 5 of the knitting machine. Its distal end 8 is located at the top portion of cylinder 1. Its proximal end 9 is outside the body of the machine and situated above the upper cylinder 3.

An optical fiber 10 is fixedly mounted parallel to an interior generating line of the cylinder 1. It is terminated by a totally reflecting prism 11 located at its upper end. Its lower end (not shown) is provided with a first luminous source.

The exit face of the prism 11 confronts a lens 13 at the distal end of the endoscope 7 such that the luminous flux from the first source is guided along the optical fiber 10 and either reflected by the prism 11 or directed to the distal lens 13.

At a portion close to its proximal end 9, the endoscope comprises a housing 4 containing a second light source and a light guide connected to the rectilinear portion of the endoscope 7. The luminous flux from this second source is guided by the internal optical system of the endoscope 7 and exits from the latter through the distal lens 13 perpendicularly to the axis 5 of the endoscope 7, where it defines a light cone 15 having a 30° cone angle.

Figure 2:
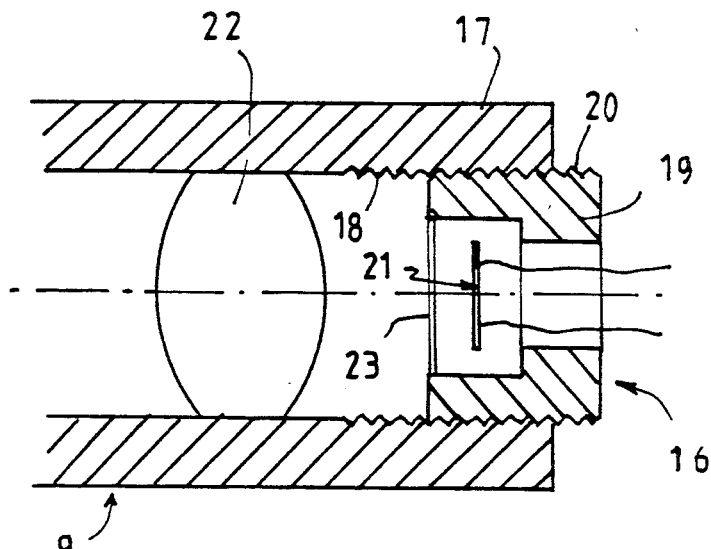
FIG. 2 is a schematic, partial cross-sectional view of the proximal end of the endoscope and of the electro-optical sensor.

The electro-optical sensor 16 is a photodiode fixed to the proximal end 9 of the endoscope 7, as shown schematically in FIG. 2. The proximal end 9 of the endoscope is terminated by a hollow cylindrical endpiece 17 whose internal surface is provided with a threading 18. The electro-optical sensor 16 is lodged inside a cylindrical mount 19 whose external surface is provided with a threading 20 made to co-operate with the threading 18 of the end piece 17. Threadings 18 and 20 have a micrometric pitch and allow the position of the mount 19 to be a fine-adjusted relative to the end piece 17.

The external surface 21 of the electro-optical sensor has an area of approximately 5 mm$^2$, corresponding to the photosensitive zone of the electro-optical sensor 16, and is accurately positioned in the image plane of the endoscope's proximal lens 22.

The front face of the mount 19 of the sensor 16 is closed by a window 23 that is transparent to luminous flux.

The electro-optical sensor 16 is connected to the processing means referring to FIG. 5, whose principle features shall now be explained. At each rotation of the knitting machine, a count-up encoder 27 delivers a number of pulses for sampling the analog signal delivered by the electro-optical sensor 16, the number of pulses being a function of the type of machine and corresponding e.g. to one sampling per half-column of stitching. A proximity sensor 28 delivers a fast signal indicating the beginning of a row. A sensor 29, synchronized with the knitting program, defines the starting point of the sock and resets the system at the first stitch of each sock. Another pair of sensors 30,31 indicates the beginning and end of the machine's alternating motions corresponding to the heel and toe portions of the socks. The complete processing system makes it possible to accurately locate the cartesian co-ordinate of each sampled signal.

The two light sources are connected to a switch alternating the power supply to each source.

The operation of the apparatus shall now be explained. For an easier understanding, the present description shall cover the case where only the luminous flux coming from the first source is used, this flux being transmitted through the knitted fabric. However, the following can also apply to a flux coming from the second source and reflected by the knitted fabric, as well as to an alternation of these two luminous fluxes.

During knitting, the knitted fabric 6 descending from the needles 2 is uniformly stretched to enter the space comprised between the prism 11 and the distal end 8 of the endoscope 7. The luminous flux 24, produced by the first luminous source and guided by the optical fiber 10, is reflected by the prism 11, whereupon it reaches the distal lens 13 of the endoscope after having passed through a given zone of the knitted fabric 6. Accordingly, the flux received by the distal lens corresponds to the image of the inspected zone of the knitted fabric 6.

The dimension of the inspected zone, i.e. the illuminated area, is adapted to the fabric's gauge to obtain an optimum level of filtering and contrast. As a typical value, an area of 6 mm×6 mm would correspond to a gauge of 14. Preferably, the area corresponds to a square whose sides contain 4 stitches.

The luminous flux received by the distal lens 13 is conveyed along the endoscope 7 up to the image plane of the proximal lens 22, corresponding to the plane where the external surface 21 of the electro-optical sensor has been positioned. The electro-optical sensor 16 thus receives the real image of the inspected zone.

Because of the rotation of the cylinder 1—and thus the knitted fabric 6—as well as the gradual lowering of the knitted fabric 6 towards the interior surface of the cylinder 1 during the knitting process, the luminous flux continuously illuminates the knitted fabric in a helical fashion. The count-up encoder causes the continual flow of data produced by the electro-optical sensor 16 to be cut up into a succession of instantaneous portions each corresponding to the real image of an inspected zone. The number of sampling pulses per rotation of the machine is a function of the loom dimension, being e.g. 400 for a machine having 200 needles.

The number of sampling pulses and the dimensions of the inspected zone are determined such that there is a partial overlap of the successively inspected zones, both in the row and column directions.

Accordingly, the processing means connected to the electro-optical sensor 16 are active during the knitting of a sock for receiving and storing successive items of data each corresponding to a specific area of the sock. These data collectively represent the mapping of the light transmitted through the sock. Each instantaneous data, termed pixel, is indexed by the row number and the half-column number. The intensity of each pixel, i.e. the grey level, is proportional to the quantity of light passing through the inspected zone. The origin of the pixel coordinates is defined by means of different sensors providing the synchronization function. Each identified pixel is encoded by a grey level and is stored as image data by the processing means.

Figure 3:
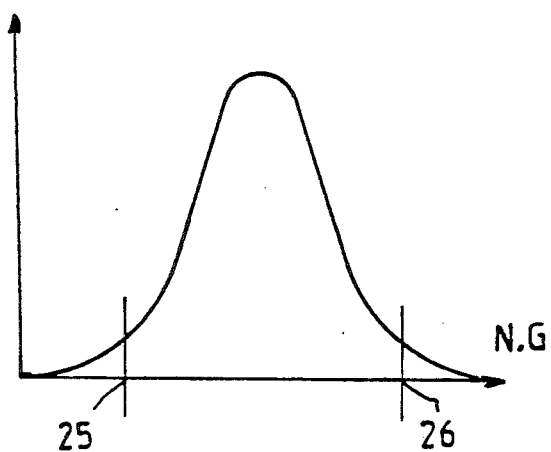
FIG. 3 shows a curve corresponding to a reference image.
Figure 4:
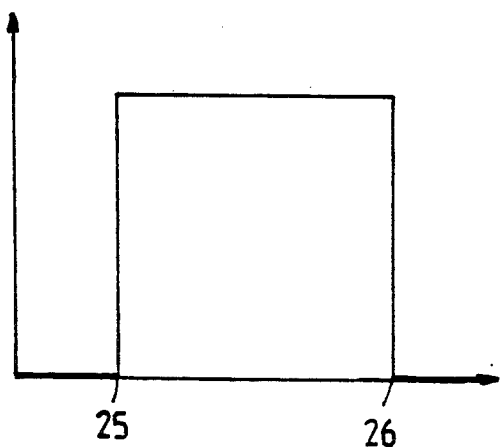
FIG. 4 is a diagram illustrating the coding function.

The grey level is encoded e.g. using a fault-free reference. FIG. 3 is a curve depicting the histogram of the grey level for the real image of a pixel for a fault-free reference sock. Using the histogram of the reference image, there is determined the minimum and maximum grey level values (25, 26) which define the characteristic limits of the image for a given probability, these values lying between a grey level corresponding to black (equal to zero) and a grey level corresponding to white (equal to 255). An encoding matrix is shown in FIG. 4 in the form of a diagram having the input grey level, corresponding to the data that is delivered by the electro-optical sensor 16, indicated along the X-axis, and having the output grey level, corresponding to the data that is reproduced and stored, indicated along the Y-axis. The grey level of the pixel, comprised between the minimum value (25) and maximum value (26) are materialised in the form of a white spot. The grey levels outside that interval are considered as flaws and are materialised in black. This encoding is effected in real time. After the knitting of the reference sock there is obtained a totally white image except for those points corresponding to the image levels that are not considered in establishing thresholds (25) and (26), and which appear in black.

When knitting all other socks, the measurements are encoded in real time in accordance with that same matrix. When the knitting of each sock under inspection is completed, there is generated an image that is filtered relative to the reference image. After this filtering, the black spots appearing on image make it possible to accurately determine the existence, nature and position of possible faults. With the use of suitable means, the identification of these faults enables a subsequent decision to be taken, e.g. the immediate stoppage of the machine in case of a detection of a continuous vertical flaw, or a repeated flaw, or a conditional stoppage upon detection of a horizontal flaw.

This control phase can be implemented in real time with decisions taken immediately during the knitting process for a sock. In that last case, the data processing system has a dual role—it simultaneously acquires a given image and processes the preceding image.

The present invention is not limited to the embodiments described in the foregoing, which were given purely as examples, but covers all other variants. In particular, the image acquisition at the distal end 9 of the endoscope 7 can be obtained by electro-optical sensors other than the photodiode e.g. by an area-array CCD or linear-array CCD.

I claim:

1. Apparatus for the detection of flaws in articles being knitted in a circular knitting machine, said apparatus comprising at least one luminous source outside the circular knitting machine, an electro-optical sensor receiving light emanating from said source after said light has been reflected by a knitted fabric or after said light has passed through said knitted fabric, and data processing means for processing data produced by said electro-optical sensor, wherein said apparatus further comprises a rectilinear endoscope fixedly mounted along a rotation axis of the knitted machine cylinder and defining an optical cone angle related to a distal lens, said lens being radially oriented towards the knitted fabric, and wherein a photo-sensitive zone of said electro-optical sensor is located above the cylinder and is substantially in an image plane of a proximal lens of said endoscope.

2. The apparatus of claim 1 wherein said distal lens of said endoscope is located directly opposite a zone of said knitted fabric, at the top portion of the cylinder of said knitting machine.

3. The apparatus of claim 1 wherein said luminous source comprises light producing means and an optical fiber terminated by a totally reflecting prism, said optical fiber being fixedly mounted inside a cylinder of said knitting machine and said prism being mounted so as to be directed radially towards said distal lens of said endoscope.

4. The apparatus of claim 1 wherein said endoscope is provided with means for transmitting luminous flux from said light producing means, at a proximal end thereof, to a distal end thereof.

5. The apparatus of claim 1 wherein it comprises:
   a first light source comprising light producing means and an optical fiber terminated by a totally reflecting prism, said optical fiber being fixedly mounted within a cylindrical portion of said knitting machine and in proximity to a wall thereof, and said prism being mounted so as to be directed radially towards a distal lens of said endoscope,
   a second light source transmitting a luminous flux from said proximal end of said endoscope, and
   switching means for switching alternately between said first light source and said second light source.

6. The apparatus of claim 1 wherein said means for processing data from said electro-optical sensor comprises synchronizing means for sampling data at a frequency that is slaved to a rotation of said knitting machine, whereby successive exploration zones of said knitted fabric overlap both in rows and in columns.

7. The apparatus of claim 6 wherein a said synchronization means comprises an incremental encoder delivering for each turn of said knitting machine, a predetermined number of pulses for sampling an analog signal produced by said electro-optical sensor, a proximity detector supplying a fast speed signal at the start of each new row; a sensor synchronized with a knitting program for resetting said apparatus at the first stitch of a knitted article.

8. The apparatus of claim 7 wherein said synchronization means comprise means for indicating the beginning and end of an alternate motion of said knitting machine.

9. The apparatus of claim 8, wherein said means for indicating the beginning and end of an alternate motion are either sensors, or signals produced as a function of said knitting program.

10. The apparatus of claim 8, wherein said means for indicating the beginning and end of an alternate motion are applied to detect heel and toe portions of items of footwear.

11. The apparatus of claim 1, wherein said electro-optical sensor is a photodiode or photo-diode array having a spectral response curve matched to the wavelength of the light source.

* * * * *